(12) United States Patent
Lv et al.

(10) Patent No.: US 12,357,458 B2
(45) Date of Patent: Jul. 15, 2025

(54) STEPWISE-CLAMPING TYPE VALVE PROSTHESIS AND DELIVERY SYSTEM THEREOF

(71) Applicant: JENSCARE SCIENTIFIC CO., LTD., Zhejiang (CN)

(72) Inventors: Shiwen Lv, Ningbo (CN); Yibin Li, Ningbo (CN); Zhi Chen, Ningbo (CN); Kan Lu, Ningbo (CN)

(73) Assignee: JENSCARE SCIENTIFIC CO., LTD., Zhejiang (CN)

( * ) Notice: Subject to any disclaimer, the term of this patent is extended or adjusted under 35 U.S.C. 154(b) by 1079 days.

(21) Appl. No.: 17/299,259

(22) PCT Filed: Nov. 28, 2019

(86) PCT No.: PCT/CN2019/121483
§ 371 (c)(1),
(2) Date: Jun. 2, 2021

(87) PCT Pub. No.: WO2020/114300
PCT Pub. Date: Jun. 11, 2020

(65) Prior Publication Data
US 2022/0023040 A1    Jan. 27, 2022

(30) Foreign Application Priority Data

Dec. 3, 2018 (CN) .......................... 201811462572.6

(51) Int. Cl.
*A61F 2/24* (2006.01)
(52) U.S. Cl.
CPC .......... *A61F 2/2436* (2013.01); *A61F 2/2409* (2013.01); *A61F 2/2418* (2013.01); *A61F 2220/0025* (2013.01)
(58) Field of Classification Search
CPC .... A61F 2/2436; A61F 2/2409; A61F 2/2418; A61F 2220/0025; A61F 2220/0008; A61F 2250/0069; A61F 2/24; A61F 2/2412
See application file for complete search history.

(56) References Cited

U.S. PATENT DOCUMENTS 8,449,599 B2    5/2013 Chau et al.
2013/0304200 A1*  11/2013 McLean ................ A61F 2/2418
                                                                  623/2.18
(Continued)

FOREIGN PATENT DOCUMENTS

CN    103079498        5/2013
CN    203943701 U     11/2014
(Continued)

OTHER PUBLICATIONS

International Search Report issued for International Patent Application No. PCT/CN2019/121483, Date of mailing: Feb. 24, 2020, 7 pages including English translation.
(Continued)

*Primary Examiner* — Melanie R Tyson
*Assistant Examiner* — Rachel S Highland
(74) *Attorney, Agent, or Firm* — Wood, Phillips, Katz, Clark & Mortimer

(57) ABSTRACT

The present application relates to a stepwise-clamping type valve prosthesis including a frame body and a clamping member. The frame body has a channel allowing blood to flow therethrough. The clamping member includes a first clamping member and a second clamping member. One end of the first clamping member is connected to the frame body, and the other end of the first clamping member is a free end. The second clamping member is connected to the first clamping member. The clamping member has three states in sequence from being restricted to being fully released. In the first state, the first clamping member and the second clamping member are both restricted and restricted. In the second state, the second clamping member is restricted, and the first clamping member extends in a radial direction of the frame body and is capable of reaching a position between a valve leaflet and a heart wall. In the third state, the second clamping member protrudes from the first clamping member and extends in a circumferential direction of the frame body and abuts against an outer surface of the frame body, so that an autologous valve leaflet and adjacent tissues are capable (Continued)

of being clamped between the second clamping member, the first clamping member, and the frame body. The contact area between the valve prosthesis and the autologous tissues can be increased, the position stability of the valve prosthesis in the heart can be improved, and the success rate of the operation can be increased.

15 Claims, 14 Drawing Sheets

(56) References Cited

U.S. PATENT DOCUMENTS

| | | |
|---|---|---|
| 2014/0222136 A1 | 8/2014 | Geist |
| 2014/0222142 A1 | 8/2014 | Kovalsky et al. |
| 2016/0242901 A1* | 8/2016 | Keren ................ A61F 2/243 |
| 2016/0296330 A1 | 10/2016 | Hacohen |
| 2017/0143481 A1* | 5/2017 | Morriss ............. A61F 2/2418 |

FOREIGN PATENT DOCUMENTS

| | | |
|---|---|---|
| CN | 205494084 U | 8/2016 |
| CN | 105943213 | 9/2016 |
| CN | 106132352 | 11/2016 |
| CN | 108882981 | 11/2018 |
| CN | 109350308 | 2/2019 |
| WO | 2011137531 | 11/2011 |
| WO | 2015188066 | 12/2015 |

OTHER PUBLICATIONS

European Search Report for European Application No. 19892150.4 issued Jan. 5, 2022.

* cited by examiner

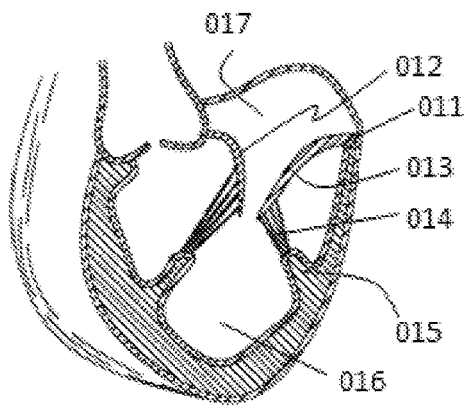
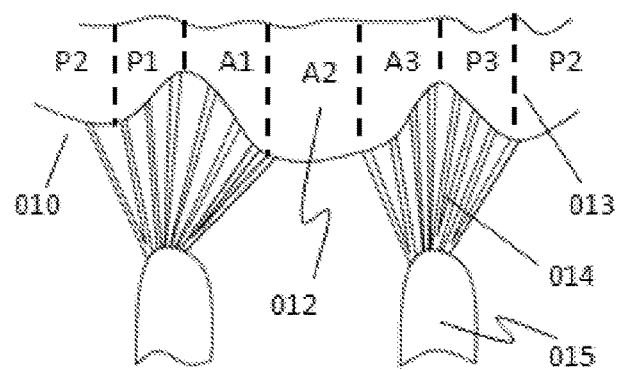
FIG. 1A
FIG. 1B
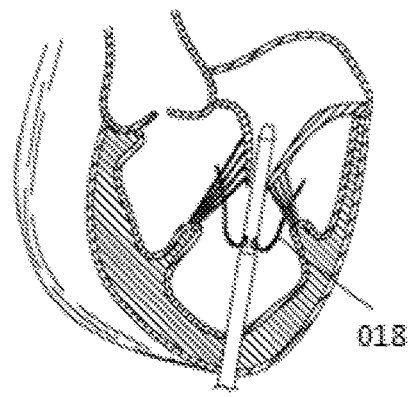
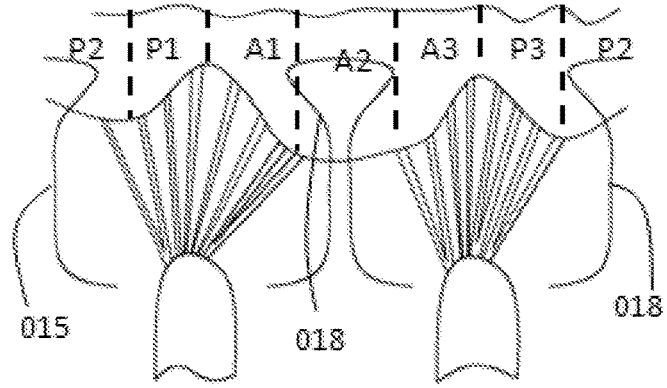
FIG. 1C (Prior Art)
FIG. 1D (Prior Art)
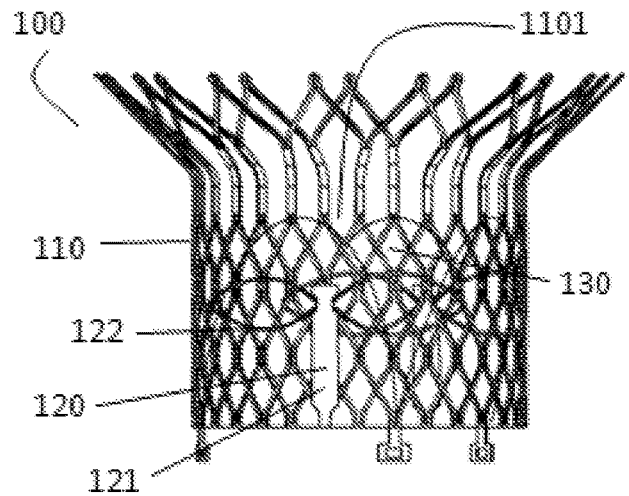
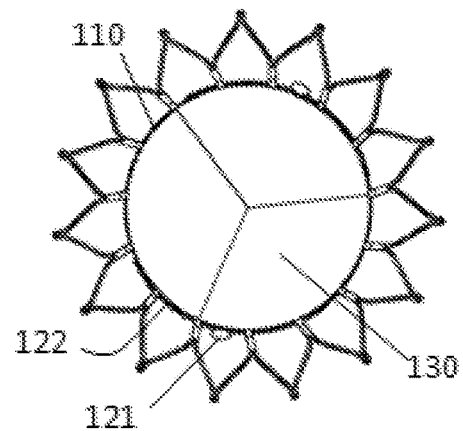
FIG. 2A
FIG. 2B

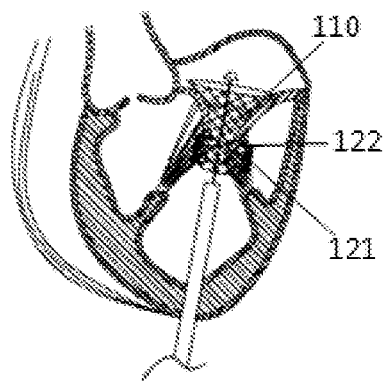
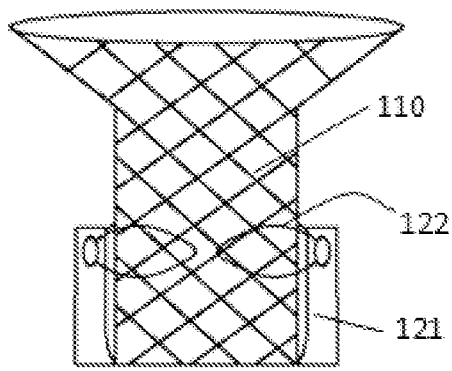
FIG. 9A    FIG. 9B
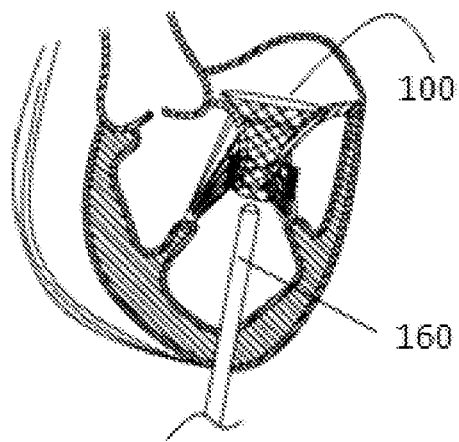
FIG. 10

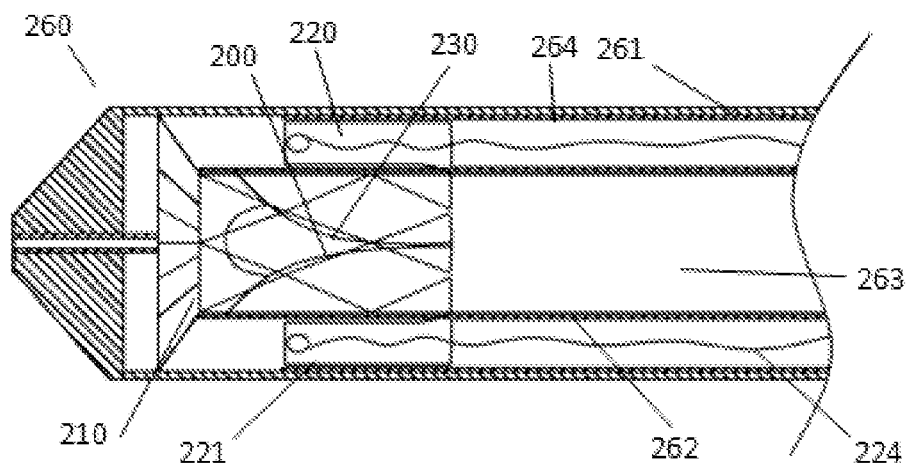
FIG. 12A
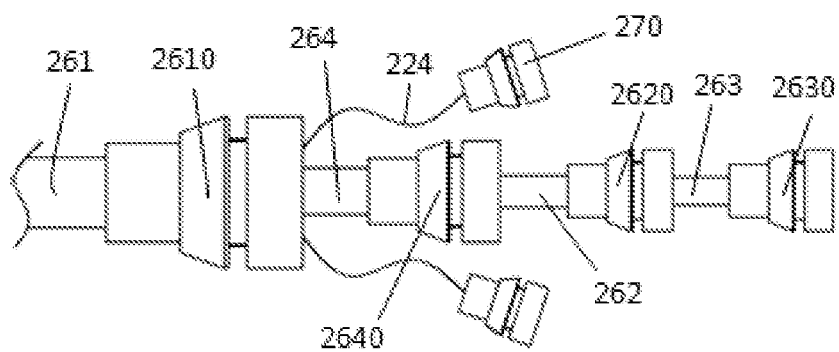
FIG. 12B
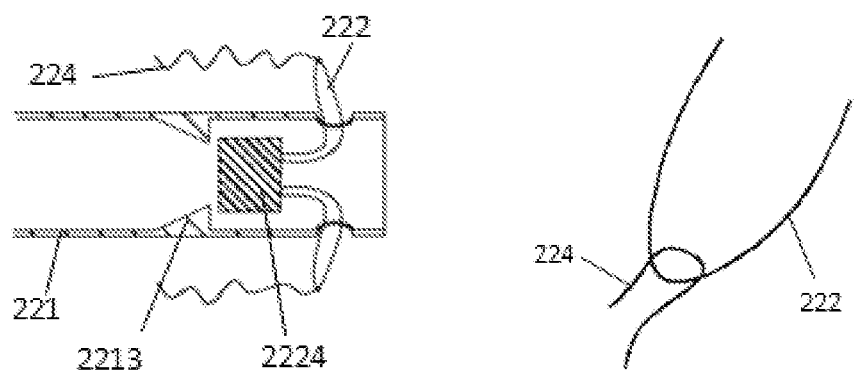
FIG. 12C
FIG. 12D

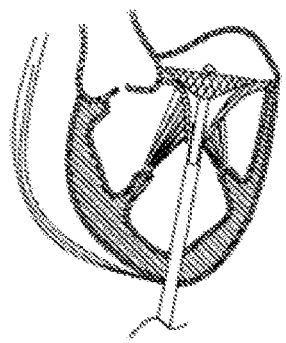 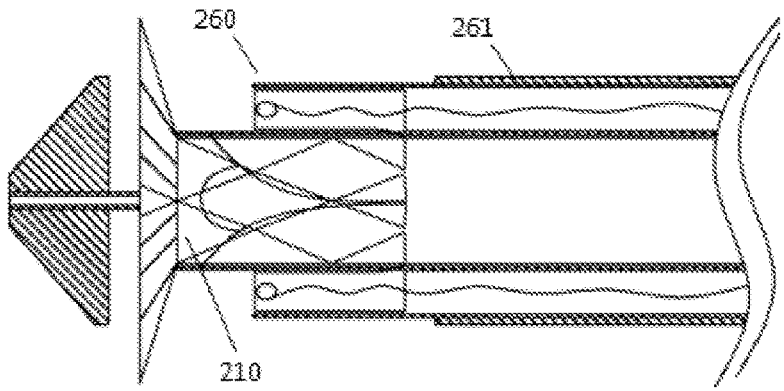
FIG. 13A    FIG. 13B
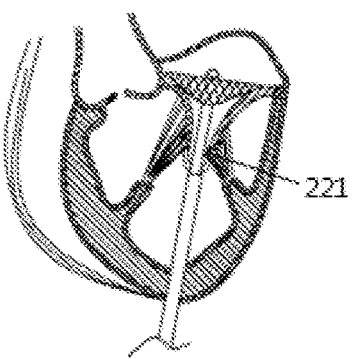 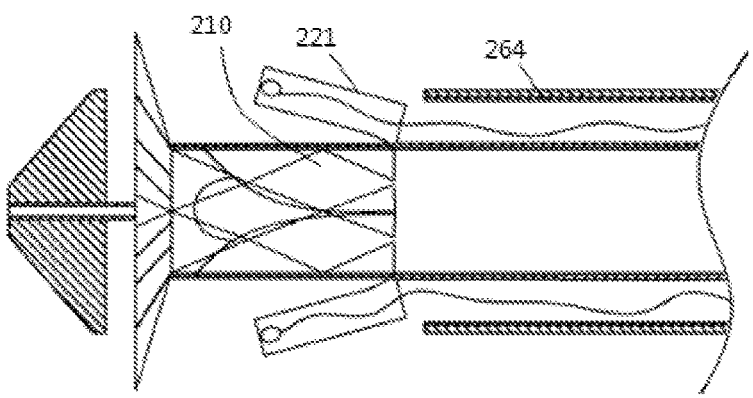
FIG. 14A    FIG. 14B
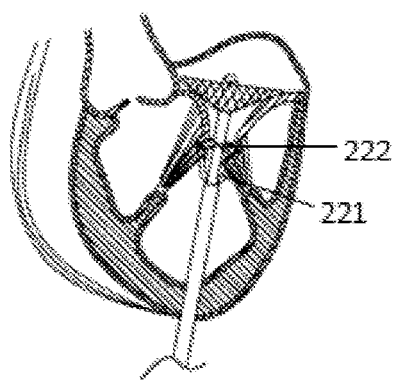 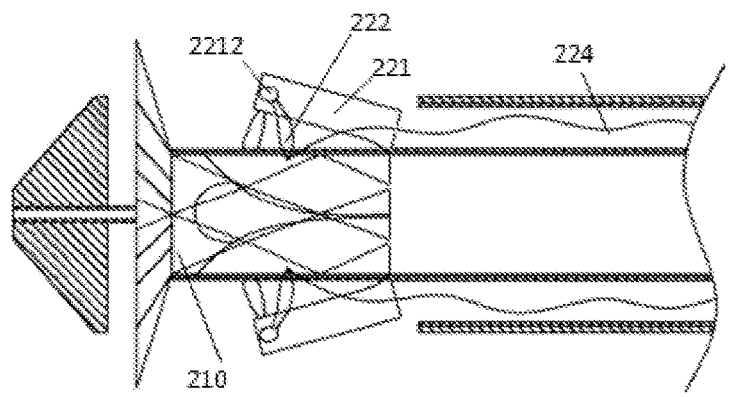
FIG. 15A    FIG. 15B

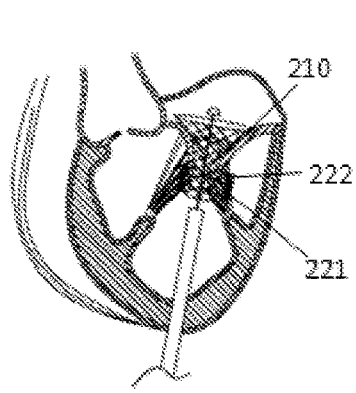 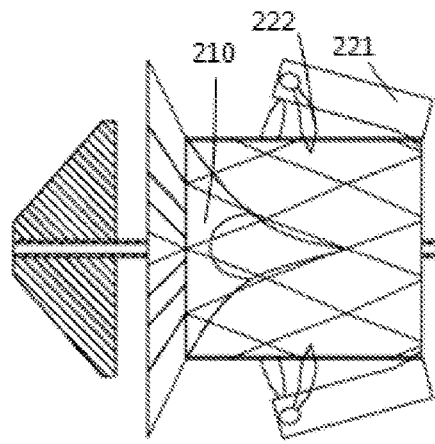
FIG. 16A                FIG. 16B
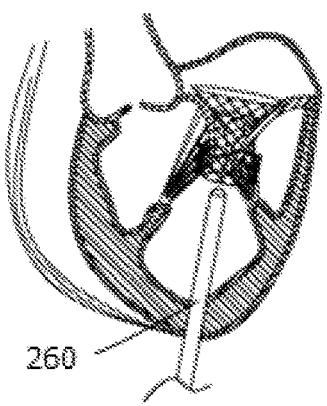
FIG. 17
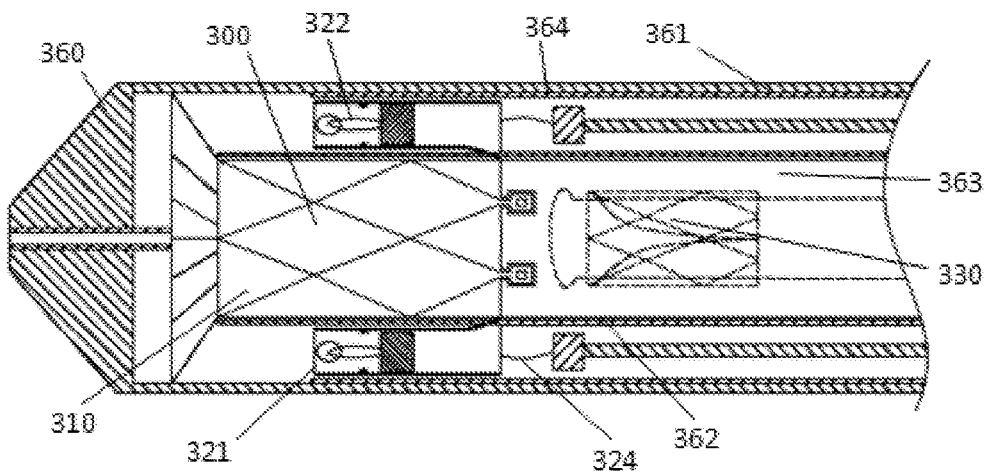
FIG. 18A

STEPWISE-CLAMPING TYPE VALVE PROSTHESIS AND DELIVERY SYSTEM THEREOF

CROSS-REFERENCE TO RELAYED APPLICATIONS

This application claims the priority of the Chinese patent application filed on Dec. 3, 2018, with the application No. 201811462572.6, titled "STEPWISE—CLAMPING TYPE VALVE PROSTHESIS AND DELIVERY SYSTEM THEREOF", which is incorporated herein by reference in its entirety. This application is a national phase under 35 U.S.C. § 120 of international patent application PCT/CN2019/121483, entitled "STEPWISE—CLAMPING TYPE VALVE PROSTHESIS AND DELIVERY SYSTEM THEREOF" filed on Nov. 28, 2019, the content of which is also hereby incorporated by reference.

FIELD

The present application relates to the field of medical devices, and in particular to a stepwise-clamping type valve prosthesis and a delivery system thereof.

BACKGROUND

The mitral valve refers to the entire structure composed of the mitral annulus, the anterior leaflet, the posterior leaflet, the chordae tendineae, the papillary muscles, the left atrium, and the left ventricle. Among them, the anterior leaflet and the posterior leaflet are separated by commissures therebetween which are respectively located anterolaterally and posteromedially. The chordae tendineae originating from the bilateral papillary muscles are inserted into the leaflets. According to the different insertion sites, the chordae tendineae are generally classified into three types: the commissure chordae, the anterior leaflet chordae, and the posterior leaflet chordae. The commissure chordae, as the name suggests, are inserted into the valve commissure and are normally fan-shaped chordae individually originated and branched from a papillary muscle, and inserted into the leaflet commissure. The anterior leaflet chordae are inserted into the free edge of the anterior leaflet to provide necessary support for the anterior leaflet of the valve, while the posterior leaflet chordae are inserted into both the free edge and the base of the posterior leaflet.

Mitral valve diseases are the most common valve diseases, which are mainly caused by the pathological alteration of the valve itself or the secondary alteration caused by the left heart system diseases. As compared to the conventional invasive surgery such as the thoracotomy, the open heart surgery, and the extracorporeal circulation, the transcatheter interventional replacement surgery has gradually become the first choice due to many advantages such as reduced difficulty of the operation, shortened recovery time of the patient, and reduced pain of the patient. However, currently there is still no perfect solution regarding how to position and fasten the replacement device at the heart and how to adapt the replacement device for different physiological structures of the valve annuluses.

The patent CN103079498A describes a transcatheter mitral valve prosthesis, which has an anchor having an atrial skirt, an annular region and a ventricular skirt. The ventricular skirt further includes a trigonal anchoring tab arranged on an anterior portion of the ventricular skirt, the trigonal anchoring tab is adapted to being anchored against a first fibrous trigon on a first side of an anterior leaflet of the patient's mitral valve, so that the anterior leaflet and adjacent chordae tendineae are captured between the trigonal anchoring tab and an anterior surface of the anchor. The ventricular skirt further includes a second trigonal anchoring tab arranged on the anterior portion of the ventricular skirt. The second trigonal anchoring tab is adapted to being anchored against a second fibrous trigon opposite the first fibrous trigon, so that the anterior leaflet and adjacent chordae tendineae are captured between the second trigonal anchoring tab and the anterior surface of the anchor. The ventricular skirt includes a posterior ventricular anchoring tab arranged on a posterior portion of the ventricular skirt. The posterior ventricular anchoring tab is adapted to being anchored over a posterior leaflet of the patient's mitral valve, so that the posterior ventricular anchoring tab is seated between the posterior leaflet and a ventricular wall of the patient's heart. According to the release method in the patent, the ventricular skirt is radially expanded thereby displacing the native mitral valve leaflets radially outward, while the valve leaflets and the adjacent chordae tendineae are captured. The problem with this design is as follows. The release of the anchoring tabs is irreversible, and it is difficult to ensure that the valve leaflets and their chordae tendineae can be clamped in the one-time release. Before the anchoring tab is released, the native valve leaflets have been partially opened and pressed by the annular region, leading to a valve leaflet disabled period, during which the natural valve leaflets have been disabled and the prosthetic valve leaflets have not yet started to work, affecting the patient's normal heart blood supply function. Limited by the release position, the release configuration, and the condition of the chordae tendineae, the anchoring tab can only perform the covering and clamping action from the region of the valve leaflets barely having chordae tendineae. For the area of the valve leaflets with the chordae tendineae, the anchoring tab will be blocked by the chordae tendineae, and thus is not ideal for its clamping stability.

In addition, the Edwards Lifesciences Corporation of the United States has disclosed a mitral valve replacement frame in patent U.S. Pat. No. 8,449,599. At least one clamping member is included at the outer surface of the frame. When the frame is restricted in the sheath, the gap between the clamping member and the outer surface of the frame is used to capture of the valve leaflet. When the frame is gradually released, the gap between the clamping member and the outer surface of the frame becomes gradually decreases, thereby capturing the valve leaflet therebetween. There are problems with this design. Firstly, the frame and the clamping member are cut as one piece, and the clamping ability of the clamping member is greatly affected by the wall thickness of the tubular material. The wall thickness of the tubular material in turn affects the supporting force of the frame. When the supporting force of the frame is too large, the tissue around the mitral valve such as the aortic valve will be pressed and the normal work thereof will be affected. It is difficult for the designer to balance the supporting force of the frame while pursuing greater clamping force of the clamping member. Secondly, the process of bending and shaping of the clamping member is complicated. Even if the shaping is successful, the fatigue resistance of the clamping member is still to be discussed. Thirdly, the clamping member only performs the covering and clamping action from the region of the valve leaflet barely having the chordae tendineae, so that the clamping stability is not ideal enough.

Fourthly, the same clamping member can clamp only one valve leaflet, and the regurgitation between the leaflets cannot be avoided.

In summary, although the technologies described above have certain effects on valve repair, as for the design of the anchoring mechanism in existing products, there is a need to provide a valve prosthesis which can be accurately positioned and especially to fully use the chordae tendineae around the autologous valve leaflets to achieve more secure anchoring.

SUMMARY

The present application provides a valve prosthesis and a delivery system thereof. In the present application, a first clamping member and a second clamping member are arranged on a frame body. When the first clamping member clamps a valve leaflet, the second clamping member extends from the first clamping member and circumferentially surrounds the adjacent chordae tendineae or the valve leaflet, so as to increase the contact area between the valve prosthesis and the autologous tissues, which is beneficial to improve the position stability of the valve prosthesis in the heart and increase the success rate of the operation.

A stepwise-clamping type valve prosthesis includes a frame body and a clamping member. The frame body has a channel allowing blood to flow therethrough. The clamping member includes a first clamping member and a second clamping member. One end of the first clamping member is connected to the frame body, and another end of the first clamping member is a free end. The second clamping member is connected to the first clamping member. The clamping member has three states in sequence from being restricted to being fully released. In the first state, the first clamping member and the second clamping member are both restricted. In the second state, the second clamping member is restricted, and the first clamping member extends in a radial direction of the frame body and is capable of reaching a position between a valve leaflet and a heart wall. In the third state, the second clamping member protrudes from the first clamping member and extends in a circumferential direction of the frame body and abuts against an outer surface of the frame body, so that a natural valve leaflet and adjacent tissues are capable of being clamped between the second clamping member, the first clamping member, and the frame body.

In one of the embodiments, the first clamping member is a hollow structure, and the second clamping member in a restricted state is arranged in the first clamping member.

In one of the embodiments, the valve prosthesis includes a second clamping member control device configured to release the second clamping member, and the second clamping member control device is arranged in the first clamping member.

In one of the embodiments, the second clamping member control device is detachably connected to the second clamping member.

In one of the embodiments, the second clamping member control device is a push rod, and the second clamping member control device is capable of pushing the second clamping member along the first clamping member. The second clamping member has a detach-preventing end, and the push rod is detachably connected to the detach-preventing end.

In one of the embodiments, the push rod is connected to the detach-preventing end through a threaded rod. By manipulating the push rod, the second clamping member is controlled to be released and retracted. When the second clamping member is completely released, the push rod can be separated from the detach-preventing end by rotating the push rod.

In one of the embodiments, the second clamping member includes two lateral wings, each of which is connected to the detach-preventing end.

In one of the embodiments, the second clamping member includes two lateral wings. One end of each of the lateral wings is connected to the first clamping member, and the other end of the each of the lateral wings is connected to the detach-preventing end. The first clamping member is provided with outlets, and the lateral wings respectively protrude from the outlets.

In one of the embodiments, a side wall of the first clamping member is provided with a stopper. The stopper is a one-way protrusion configured to restrict the movement of the detach-preventing end, such that the detach-preventing end cannot move back after passing the protrusion.

In one of the embodiments, the lateral wings have a shape with a single or multiple continuous arcs. The advantage of this design is that the arc-shaped end can prevent cutting and bleeding the heart wall tissue.

In one of the embodiments, the second clamping member is arranged on an outer surface of the first clamping member.

In one of the embodiments, the valve prosthesis includes a second clamping member control device configured to release the second clamping member, and the second clamping member control device is arranged outside the first clamping member.

In one of the embodiments, the second clamping member control device is detachably connected to the second clamping member.

In one of the embodiments, the second clamping member control device is a wire.

In one of the embodiments, the second clamping member is bound to the surface of the first clamping member by the wire. The second clamping member can be released by loosening a releasable knot, drawing the wire, or cutting the wire.

In one of the embodiments, ends of the second clamping member are detachably connected to the wires. By pulling the wires, the lateral wings of the second clamping member are moved and released.

In one of the embodiments, the second clamping member control device is a sleeve.

In one of the embodiments, the frame body is a self-expanding frame made of a shape memory material or an elastic material, such as nickel-titanium shape memory alloy.

In one of the embodiments, the frame body is integrally carved from a shape memory material tube, for example, a nickel-titanium shape memory alloy tube.

In one of the embodiments, a valve leaflet body is arranged in the frame body. The valve leaflet body is pre-fixed in the frame body, or the valve leaflet body is released into the frame body after the frame body is completely released.

A delivery system of the stepwise-clamping type valve prosthesis includes the stepwise-clamping type valve prosthesis, an outer sheath, a frame sheath, a frame sheath core, and a clamping member sheath. The stepwise-clamping type valve prosthesis includes a frame body and a clamping member. The clamping member includes a first clamping member and a second clamping member. One end of the first clamping member is connected to the frame body, and another end of the first clamping member is a free end. The second clamping member is connected to the first clamping member. The frame sheath and the clamping member sheath are arranged in the outer sheath. The clamping member sheath is arranged between the outer sheath and the frame sheath. The frame body is arranged at a distal end of the frame sheath and partly located outside the frame sheath. The frame sheath core is arranged in the frame sheath. The second clamping member control device is arranged in the clamping member sheath. The first clamping member that is compressed is located at a distal end of the clamping member sheath. A proximal end of the outer sheath is connected to an outer sheath operating member. A proximal end of the frame sheath is connected to a frame sheath operating member. A proximal end of the frame sheath core is connected to a frame sheath core operating member. A proximal end of the clamping member sheath is connected to a clamping member sheath operating member. One end of the second clamping member control device is connected to a second clamping member control device operating member. The first clamping member and the second clamping member have three states in sequence from being restricted to being fully released. In the first state, the first clamping member and the second clamping member are both restricted. In the second state, by operating the clamping member sheath operating member, the first clamping member is extended in the radial direction of the frame body and is capable of reaching the position between a valve leaflet and a heart wall. In the third state, by operating the second clamping member control device operating member, the second clamping member is protruded from the first clamping member and circumferentially surrounds and abuts against the outer surface of the frame body, so that a natural valve leaflet and adjacent tissues are capable of being clamped between the second clamping member, the first clamping member and the frame body.

In one of the embodiments, in the first state, the first clamping member is restricted in the clamping member sheath, and the second clamping member is restricted in the first clamping member.

In one of the embodiments, in the first state, the first clamping member is restricted in the sheath of the clamping member, and the second clamping member is restricted outside the first clamping member.

In one of the embodiments, the second clamping member control device is detachably connected to the second clamping member.

In one of the embodiments, the second clamping member control device is detachably connected to the second clamping member control device operating member.

In one of the embodiments, the distal end of the clamping member sheath and the distal end of the second clamping member control device are both flexible.

In one of the embodiments, an opening angle is predetermined between the first clamping member and the frame body.

Compared with the prior art, the advantages of the embodiments of the present application are as follows:

1. Different from the downstream clamping of the valve leaflet (which can only axially clamp from the region of the valve leaflet barely having the chordae tendineae), the clamping member in the embodiments of the present application can not only clamp the autologous valve leaflet, but also allow the second clamping member to deploy along the frame body in a natural state, which realizes the double clamping of the valve leaflet and the chordae tendineae, increasing the clamping area, improving the anchoring effect, and effectively reducing the regurgitation between adjacent valve leaflets.

2. In the embodiments of the present application, the first clamping member and the second clamping member are provided. The first clamping member reaches the back of the autologous valve leaflet, and then the second clamping member extends from the first clamping member. This stepwise clamping method allows the second clamping member to access the designated working position without being blocked, avoiding contact with the autologous tissues during the access, thereby reducing the damage to the body tissues. Moreover, the clamping area is increased when the second clamping member is fully released, which enhances the clamping effect.

3. Different from the prior art that the clamping body is released integrally, the first clamping member and the second clamping member in the embodiments of the present application are stepwise released in a reversible manner. When the first clamping member has not been completely released from the clamping member sheath, the clamping member sheath can be pushed to make the first clamping member re-enter the sheath. When the second clamping member has not been completely detached from the second clamping member control device, the second clamping member control device can be controlled to make the second clamping member restore the restricted state.

4. Compared with the prior art, an outlet is provided on the first clamping member in the embodiments of the present application. The position of the outlet can determine the deployment position of the second clamping member, so as to accurately release the second clamping member, which is convenient for the surgeon to operate while greatly improving the safety.

5. Compared with the prior art, the second clamping member in the embodiments of the present application can be in contact with the autologous chordae tendineae in a large area. When the second clamping member is released, the lateral wings are inserted into the gaps in the chordae tendineae, which can prevent the second clamping member from detaching from the autologous chordae tendineae and avoid sliding of the valve prosthesis in the human body.

6. The distal end of the clamping member sheath and the distal end of the push rod are both flexible in the embodiments of the present application. This design is to make the distal ends of the clamping member sheath and the second clamping member control device adaptable to the deformation of the clamping member.

BRIEF DESCRIPTION OF THE DRAWINGS

FIGS. 1A to 1D are schematic views showing the release and clamping of an existing product, wherein FIG. 1A is a schematic structural view of a heart, FIG. 1B is a schematic structural view of a deployed mitral valve, and FIGS. 1C and 1D are schematic views showing the release and clamping positions of the existing product.

FIGS. 2A and 2B are schematic structural views of an embodiment of the present application, wherein FIG. 2B is a top view of FIG. 2A.

FIGS. 5A to 5D are schematic views of an embodiment of a delivery system of the present application, wherein FIG. 5B is a cross-sectional view of FIG. 5A.

FIG. 6A, FIG. 6B, FIG. 7A, FIG. 7B, FIG. 8A, FIG. 8B, FIG. 9A, FIG. 9B and FIG. 10 are schematic views of release steps of an embodiment of the present application.

FIGS. 12A to 12D are schematic views of another embodiment of the delivery system of the present application.

FIG. 13A, FIG. 13B, FIG. 14A, FIG. 14B, FIG. 15A, FIG. 15B, FIG. 16A, FIG. 16B, and FIG. 17 are schematic views of release steps of another embodiment of the present application.

FIGS. 18A to 18D are schematic structural views of a third embodiment of the present application.

DETAILED DESCRIPTION

Figure 3:
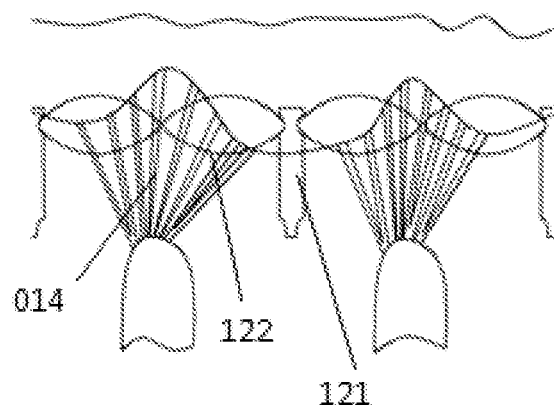
FIG. 3 is a schematic view showing the clamping effect of a valve prosthesis of the present application.

In order to make the objects, technical solutions, and advantages of the present application more clear and understandable, the present application will be further described in detail as below with reference to the drawings and embodiments.

The distal end described in the present application refers to the end farther from the apex of the heart, and the proximal end described in the present application refers to the end nearer to apex of the heart.

Example 1

Referring to FIG. 1A which shows the left atrium 017 and the left ventricle 016 of the left half of a heart, the blood can flow unidirectionally from the left atrium 017 into the left ventricle 016. The mitral valve of the heart is located at the communicating area between the left atrium 017 and the left ventricle 016. The mitral valve includes the mitral annulus 011, the anterior leaflet 012, the posterior leaflet 013, the chordae tendineae 014, and the papillary muscles 015. The anterior leaflet 012 and the posterior leaflet 013 are respectively connected to the corresponding papillary muscles 015 via their own chordae tendineae 014. In a healthy heart organ, when the papillary muscles 015 contract to tense the chordae tendineae 014, the mitral valve is in an open state; and when the papillary muscles 015 relax to loose the chordae tendineae 014, the mitral valve is in a closed state.

Referring to FIG. 1B, the mitral valve is generally divided by the person skilled in the art into several regions, in which anterior leaflet 012 (A1, A2, A3) and the posterior leaflet 013 (P1, P2, P3) are separated by commissures therebetween which are respectively located anterolaterally and posteromedially. The chordae tendineae mainly distributed at the commissures between the anterior leaflet 012 and the posterior leaflet 013. Normally, the convex portions of the anterior leaflet 012 and the posterior leaflet 013 have no chordae tendineae bound thereto, and thus are the main areas of the mitral valve to connect the artificial valve prosthesis.

Referring to FIG. 1C and FIG. 1D, all of the existing products, such as Edwards's TIARA and Neovasc's FORTIS, adopt anchoring tab structures 018 fixed on a frame and approaching the valve annulus from the free portions of the valve leaflets. Further, referring to FIG. 1D, the anchoring tabs 108, both during inserting to the back of the valve leaflets and at the final clamping positions, substantially bypass the chordae tendineae (the anchoring tab structures 018 are roughly located at the regions A2 and P2). As the clamping area is limited, the nearby chordae tendineae structures are underutilized, making the anchoring not secure and reliable enough.

Referring to FIGS. 2A and 2B, a stepwise-clamping type valve prosthesis 100 of the present application includes a frame body 110 and at least one clamping member 120. The frame body 110 has a channel 1101 allowing blood to flow therethrough. The clamping member 120 includes a first clamping member 121 and a second clamping member 122. One end of the first clamping member 121 is connected to the frame body 110, and the other end of the first clamping member 121 is a free end. The second clamping member 122 is connected to the first clamping member 121. The clamping member 120 has three states in sequence from being restricted to being fully released. In the first state, the first clamping member 121 and the second clamping member 122 are both restricted. In the second state, the second clamping member 122 is restricted, and the first clamping member 121 extends in the radial direction of the frame body 110 from the anterior leaflet, the posterior leaflet, or the commissure between the anterior leaflet and the posterior leaflet of the mitral valve, to reach the position between the valve leaflet and the heart wall. In the third state, the second clamping member 122 protrudes from the first clamping member 121 and extends in the circumferential direction of the frame body 110 and abuts against the outer surface of the frame body 110. The autologous valve leaflet and adjacent tissues are clamped between the second clamping member 122, the first clamping member 121, and the frame body 110. In the present application, the first clamping member 121 and the second clamping member 122 are provided. The first clamping member 121 reaches the back of the autologous valve leaflet, and then the second clamping member 122 extends from the first clamping member 121. This stepwise clamping method allows the second clamping member 122 to access the designated working position without being blocked, avoiding contact with the autologous tissues during the access, thereby reducing the damage to the body tissues. Moreover, the clamping area is increased when the second clamping member 122 is fully released, which enhances the clamping effect.

In an embodiment, the valve prosthesis 100 further includes a valve leaflet body 130. The valve leaflet body 130 allows blood to pass in one direction and blocks its regurgitation. The valve leaflet body 130 is pre-fixed inside the frame body 110. The valve leaflet body 130 is made of an animal tissue or high molecular polymers. In an embodiment, the animal tissue is porcine pericardium, bovine pericardium, horse pericardium, or the like, and the high molecular polymer is polytetrafluoroethylene, polyurethane, or silica gel. The frame body 110 is a self-expanding frame, made of a shape memory material or an elastic material, such as nickel-titanium shape memory alloy. In an embodiment, the frame body 110 is integrally carved from a shape memory material tube, for example, a nickel-titanium shape memory alloy tube.

In the present embodiment, the valve prosthesis is used to clamp the mitral valve. The number of the first clamping members 121 is two. The second clamping members 122 circumferentially surrounding the frame body 110 are extended from the first clamping members 121. It is worth mentioning that the second clamping member 122 extends from both sides of the first clamping member 121 along the circumference of the frame body 110, so that a relatively large clamping area can be obtained, and the second clamping member 122 is symmetrically distributed on both sides of the first clamping member 121.

Referring to FIG. 3, compared with the prior art, the second clamping member 122 in the present application has a lateral wing structure, which can be in contact with the autologous chordae tendineae in a large area. When the first clamping member 121 reaches the position between the valve leaflet and the ventricular wall, the second clamping member 122 extends from both sides of the first clamping member 121, not only capable of clamping the autologous valve leaflet 012, but also capable of transversely clamping the chordae tendineae 014. In the actual release process, the second clamping member 122 can be partially inserted into the gaps in the autologous chordae tendineae 014, or entirely located at the heart wall side of the chordae tendineae 014, which can increase the difficulty of detaching the second clamping member 122 from the autologous chordae tendineae, thereby avoiding sliding of the valve prosthesis in the body and achieving a good clamping and securing effect.

Figure 4A:
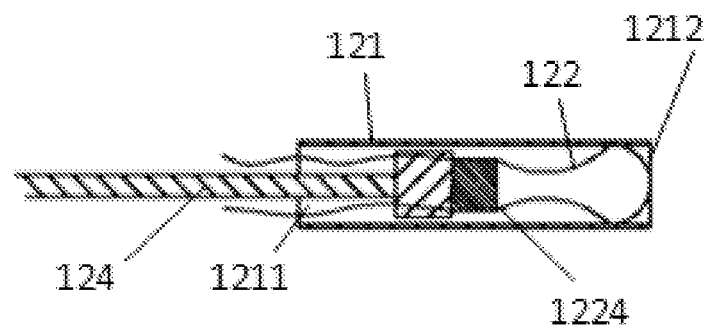
FIGS. 4A to 4C are schematic views of various embodiments of the valve prosthesis of the present application.

Referring to FIG. 4A, as an embodiment, the first clamping member 121 is a hollow structure and has an inlet 1211 and an outlet 1212. The second clamping member 122 in a restricted state is arranged in the first clamping member 121. The valve prosthesis 100 further includes a second clamping member control device 124 configured to release the second clamping member 122. The second clamping member control device 124 is a push rod, the distal end of which can enter the first clamping member 121 through the inlet 1211 and is arranged in the first clamping member 121. Pushing the push rod can release the second clamping member 122 from the outlet 1212 of the first clamping member 121. The second clamping member 122 is pre-shaped to have a structure that can surround the outer surface of the frame body 110. The second clamping member control device 124 is detachably connected to the second clamping member 122. Specifically, the second clamping member 122 has a detach-preventing end 1224, and the push rod 124 is detachably connected to the detach-preventing end 1224 through a rope buckle.

Figure 4B:
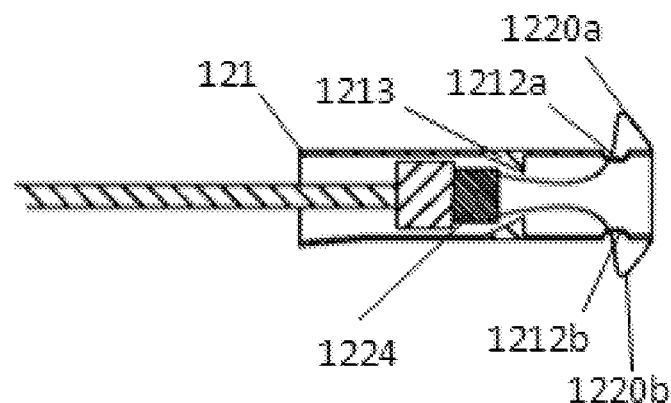

Referring to FIG. 4B, as an embodiment, the second clamping member 122 includes two lateral wings. The lateral wings 1220a and 1220b have a shape with single or multiple continuous arcs. The advantage of this design is that the arc-shaped end can prevent cutting and bleeding the heart wall tissue. One end of each of the lateral wings 1220a and 1220b is connected to the first clamping member 121, and the other end is connected to the detach-preventing end 1224. The first clamping member 121 is provided with outlets 1212a and 1212b. The lateral wings 1220a and 1220b respectively protrudes from their corresponding outlets 1212a and 1212b. Compared with the prior art, the positions of the outlets 1212a and 1212b in the present embodiment can determine the deployment position of the second clamping member 122, so as to accurately release the second clamping member 122, which is convenient for the surgeon to operate while greatly improving the safety. The inner wall of the first clamping member 121 is provided with a stopper 1213. The stopper 1213 is a one-way protrusion. The detach-preventing end 1224 cannot move back after passing the protrusion 1213. The size of the detach-preventing end 1224 is larger than the sizes of the outlets 1212a and 1212b.

Figure 4C:
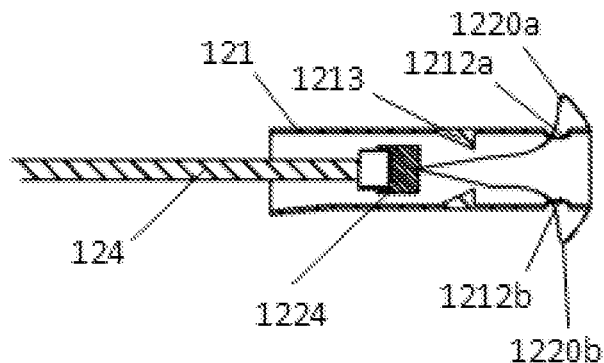
Figure 5A:
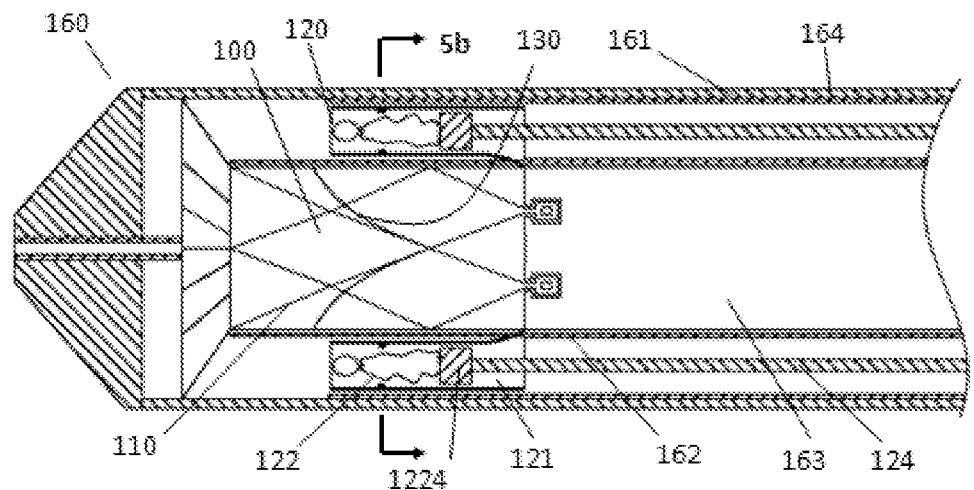
Figure 5B:
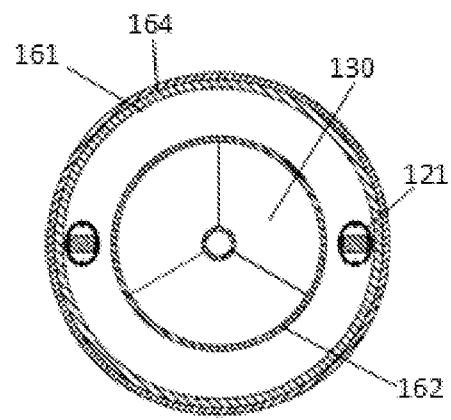
Figure 5C:
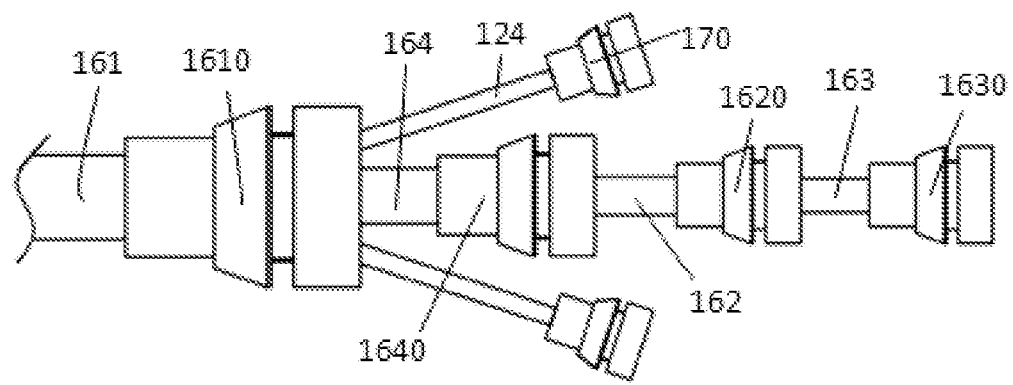
Figure 5D:
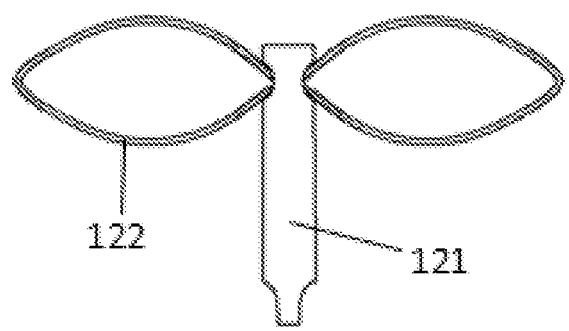

Referring to FIG. 4C, as an embodiment, the second clamping member 122 includes two lateral wings. The proximal ends of the lateral wings 1220a and 1220b are both connected to the detach-preventing end 1224. The push rod 124 is connected to the detach-preventing end 1224 through a threaded rod. When the push rod 124 is connected to the detach-preventing end 1224, by manipulating the push rod 124, the lateral wings 1220a and 1220b can be controlled to respectively protrude and retract through the corresponding outlets 1212a and 1212b. After the detach-preventing end 1224 passes the stopper 1213, the second clamping member 122 is completely released. At this time, the push rod 124 can be separated from the detach-preventing end 1224 by rotating the push rod 124. The push rod 124 can be withdrawn from the first clamping member 121 and taken away from the human body by a delivery device.

In another embodiment, the push rod 124 is only in contact with the detach-preventing end 1224. In the process of releasing the second clamping member 122, the push rod 124 can provide a pushing force to the detach-preventing end 1224, but cannot realize the pulling-back operation of the detach-preventing end 1224.

Referring to FIGS. 5A to 5D, in order to achieve the above-described technical solutions, the present application also provides a delivery system 160 for the stepwise-clamping type valve prosthesis. The delivery system includes a stepwise-clamping type valve prosthesis 100, an outer sheath 161, a frame sheath 162, a frame sheath core 163, and a clamping member sheath 164. The stepwise-clamping type valve prosthesis 100 includes a frame body 110 and at least one clamping member 120. The frame body 110 has a channel 1101 allowing blood to flow therethrough. The clamping member 120 includes a first clamping member 121 and a second clamping member 122. One end of the first clamping member 121 is connected to the frame body 110, and the other end of the first clamping member 121 is a free end. The second clamping member 122 is connected to the first clamping member 121. The valve prosthesis 100 further includes a valve leaflet body 130. The valve leaflet body 130 allows blood to pass in one direction and blocks its regurgitation. The valve leaflet body 130 is pre-fixed inside the frame body 110. The frame sheath 162 and the clamping member sheath 164 are arranged in the outer sheath 161. The clamping member sheath 164 is arranged between the outer sheath 161 and the frame sheath 162. The frame body 110 is arranged at the distal end of the frame sheath 162 and partly located outside the frame sheath 162. The frame sheath core 163 is arranged in the frame sheath 162. The second clamping member control device 124 is a push rod, which is arranged in the clamping member sheath 164. The first clamping member 121 after being compressed is located at the distal end of the clamping member sheath 164. The proximal end of the outer sheath 161 is connected to an outer sheath operating member 1610. The proximal end of the frame sheath 162 is connected to a frame sheath operating member 1620. The proximal end of the frame sheath core 163 is connected to a frame sheath core operating member 1630. The proximal end of the clamping member sheath 164 is connected to a clamping member sheath operating member 1640. One end of the push rod 124 is connected to a second clamping member control device operating member 170, and the other end of the push rod 124 is detachably connected to the detach-preventing end 1224 of the second clamping member 122 in the first clamping member 121.

The first clamping member 121 and the second clamping member 122 have three states from being restricted to being fully released. In the first state, the first clamping member 121 is restricted in the clamping member sheath 164, and the second clamping member 122 is restricted in the first clamping member 121. In the second state, by operating the clamping member sheath operating member 1640, the first clamping member 121 is extended in the radial direction of the frame body 110 to reach the position between the valve leaflet and the heart wall. In the third state, by operating the second clamping member control device operating member 170, the second clamping member 122 is protruded from the first clamping member 121 and circumferentially surrounds and abuts against the outer surface of the frame body 110, and the autologous valve leaflet and adjacent tissues are clamped between the second clamping member 122, the first clamping member 121 and the frame body 110.

The operation process of the valve prosthesis delivery system 160 in the present application is described step by step as follows.

Figure 6A:
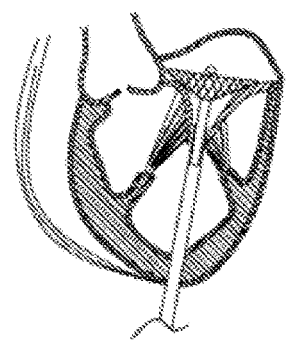
Figure 6B:
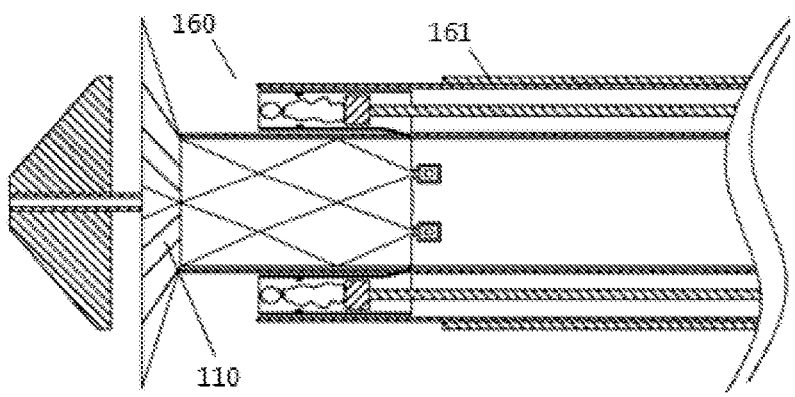

(1) Referring to FIGS. 6A to 6B, Step 1: Withdrawing the Outer Sheath

After the valve prosthesis is delivered to the target site of the patient, the outer sheath operating member 1610 is operated to make the outer sheath 161 slide in the axial direction toward the proximal end until the distal end portion of the frame body 110 is released and deployed. The deployed portion of the frame body 110 is adjusted such that it is positioned on the patient's valve annulus and abuts against the atrial tissue.

Figure 7A:
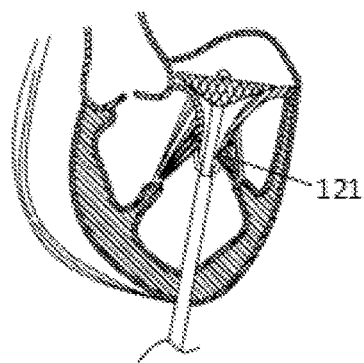
Figure 7B:
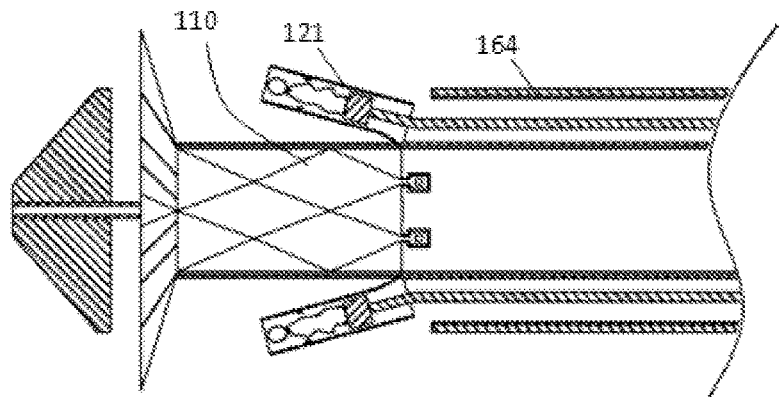

(2) Referring to FIGS. 7A to 7B, Step 2: Releasing the First Clamping Member

The clamping member sheath operating member 1640 is operated to move the clamping member sheath 164 in the axial direction toward the proximal end until the first clamping member 121 is released. An opening angle is predetermined between the first clamping member 121 and the frame body 110. After the clamping member sheath 164 is removed, the first clamping member 121 is deviated to the predetermined angle from the frame body 110. At this time, the first clamping members 121 reach the positions between the leaflets and the ventricular wall from the region A2 of the anterior leaflet and the region P2 of the posterior leaflet (as shown in FIG. 1B).

Figure 8A:
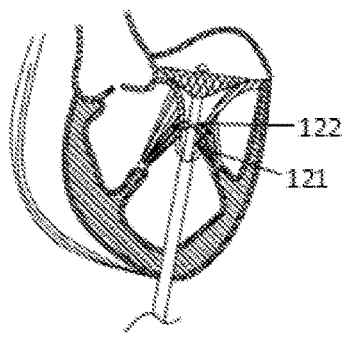
Figure 8B:
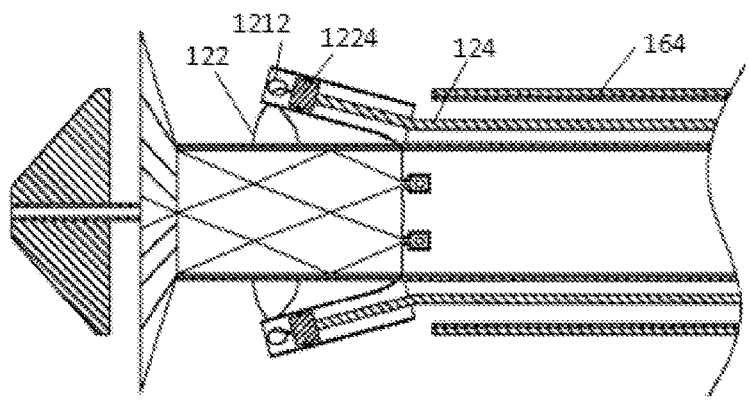

(3) Referring to FIGS. 8A to 8B, Step 3: Releasing the Second Clamping Member

The second clamping member control device operating member 170 as a whole is pushed to move the push rod 124 toward the distal end. The push rod 124 further pushes the detach-preventing end 1224. The second clamping member 122 connected to the detach-preventing end 1224 is moved with the detach-preventing end 1224 and protruded out from the outlet 1212. The second clamping member control device operating member 170 is continuously pushed until the detach-preventing end 1224 finally passes the stopper, then the second clamping member 122 is completely released. At this time, the first clamping member 121 has reached the position between the valve leaflet and the ventricular wall, so that the obstacle to the protrusion of the second clamping member 122 is greatly reduced. The second clamping member 122 surrounds the frame body 110 with its two lateral wings in the predetermined shape. The valve leaflet and the chordae tendineae are partially clamped between the second clamping member 122 and the outer surface of the frame body 110. It is worth mentioning that the push rod 124 is detachably connected to the detach-preventing end 1224. If the deviation of the second clamping member 122 occurs during the release process, the second clamping member control device operating member 170 can be pulled to make the second clamping member 122 re-enter the first clamping member 121, which greatly improves the success rate of surgery. Different from the prior art that the clamping body is released integrally, the first clamping member 121 and the second clamping member 122 in the present application are stepwise released in a reversible manner. When the first clamping member 121 has not been completely released from the clamping member sheath 164, the clamping member sheath 164 can be pushed to make the first clamping member 121 re-enter the sheath. When the second clamping member 122 has not been completely detached from the second clamping member control device 124, the second clamping member control device 124 can be controlled to make the second clamping member 122 restore the restricted state.

(4) Referring to FIGS. 9A to 9B, Step 4: Releasing the Frame Body Completely

The frame sheath operating member 1620 is operated to make the frame sheath 162 slide in the axial direction toward the proximal end, so that the frame body 110 is completely released and deployed. The patient's valve leaflets and adjacent chordae tendineae are clamped between the first clamping members 121, the second clamping members 122, and the frame body 110.

(5) Referring to FIG. 10, Step 5: Withdrawing the Delivery System

The outer sheath operating member 1610 is operated to make the outer sheath 161 slide in the axial direction toward the distal end until the distal end of the outer sheath 161 touches a guiding tip, and then the delivery system 160 is withdrawn from the human body via the apex of the heart.

Example 2

Figure 11A:
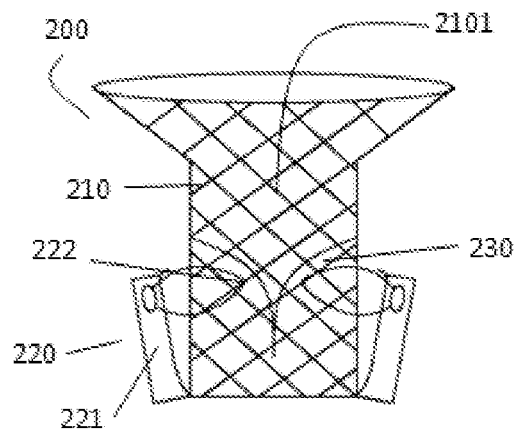
FIGS. 11A and 11B are schematic structural views of another embodiment of the present application.
Figure 11B:
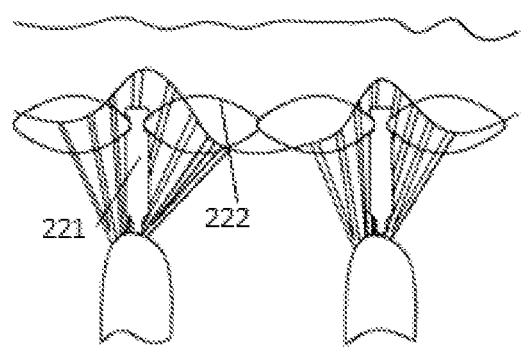
Figure 11C:
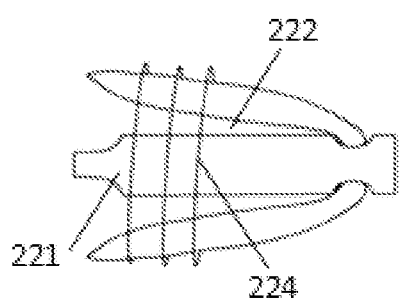
FIGS. 11C to 11F are schematic views of various embodiments of a clamping member of the present application.

Referring to FIGS. 11A to 11C, a stepwise-clamping type valve prosthesis 200, as another embodiment, includes a frame body 210 and two clamping members 220. The frame body 210 has a channel 2101 allowing blood to flow therethrough. The clamping members 220 each include a first clamping member 221 and a second clamping member 222. One end of the first clamping member 221 is connected to the frame body 210, and the other end of the first clamping member 221 is a free end. The second clamping member 222 is connected to the first clamping member 221. The clamping members 220 have three states in sequence from being restricted to being fully released. In the first state, the first clamping member 221 and the second clamping member 222 are both restricted. In the second state, the second clamping member 222 is restricted, and the first clamping member 221 extends in the radial direction of the frame body 210 from the anterior leaflet, the posterior leaflet, or the commissure between the anterior leaflet and the posterior leaflet of the mitral valve (as shown in FIG. 11B), to reach the position between the valve leaflet and the heart wall. In the third state, the second clamping member 222 protrudes from the first clamping member 221 and extends in the circumferential direction of the frame body 110 and abuts against the outer surface of the frame body 110. The autologous valve leaflets and adjacent tissues are clamped between the second clamping member 222, the first clamping member 221, and the frame body 210. Different from the downstream clamping of the valve leaflet (which can only axially clamp from the region of the valve leaflet barely having the chordae tendineae), the clamping members 220 in the present application can not only clamp the autologous valve leaflets, but also allow the second clamping member 222 to deploy along the frame body 210 in a natural state, which realizes the double clamping of the valve leaflets and the chordae tendineae, increasing the clamping area, improving the anchoring effect, and effectively reducing the regurgitation between adjacent valve leaflets.

The valve prosthesis 200 further includes a valve leaflet body 230. The valve leaflet body 230 is pre-fixed inside the frame body 210. The second clamping member 222 is arranged outside the first clamping member 221 and is in a restricted state. The valve prosthesis 200 includes a second clamping member control device 224 configured to release the second clamping member 222. The second clamping member control device 224 is arranged outside the first clamping member 221. The second clamping member control device 224 is detachably connected to the second clamping member 222. Further, the second clamping member control device 224 is a wire. The second clamping member 222 is bound to the surface of the first clamping member 221 by the wire. The second clamping member 222 is released by loosening a releasable knot, drawing the wire, or cutting the wire.

Figure 11D:
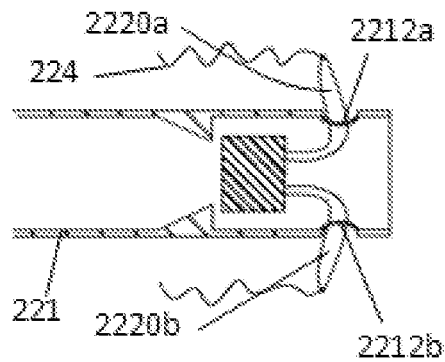

Referring to FIG. 11D, as an embodiment, the second clamping member 222 includes two lateral wings. The first clamping member 221 is provided with outlets 2212a and 2212b. Ends of the second clamping member 222 are detachably connected to the wires 224. By pulling the wires 224, the lateral wings 2220a and 2220b respectively protrude from their corresponding outlets 2212a and 2212b.

Figure 11E:
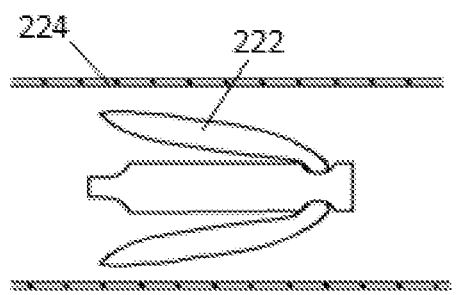
Figure 11F:
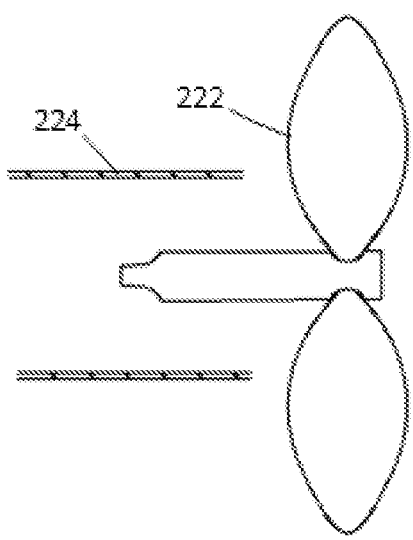
Figure 18B:
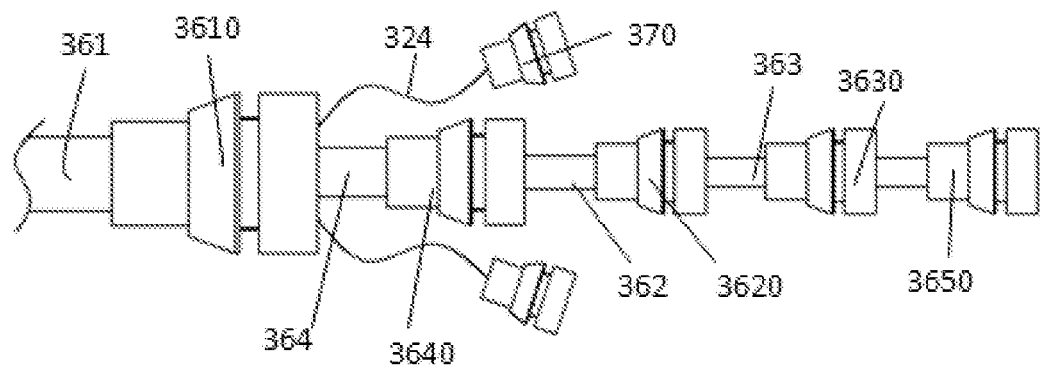
Figure 18C:
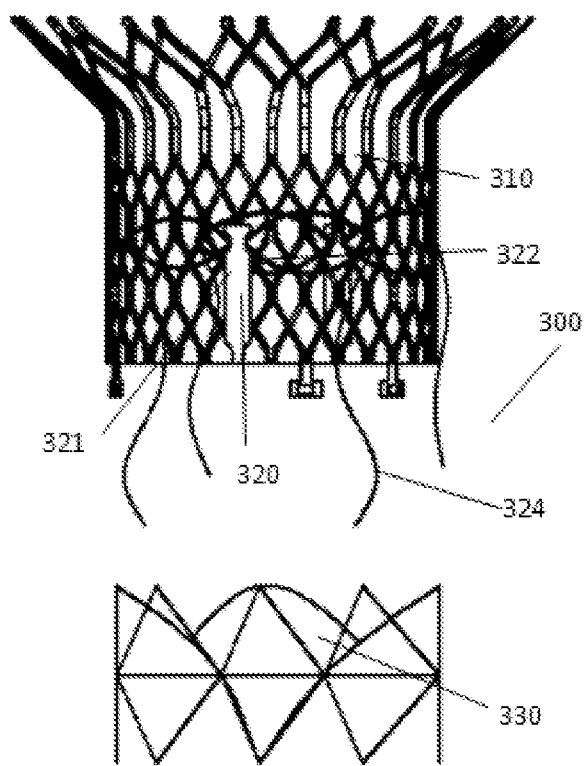
Figure 18D:
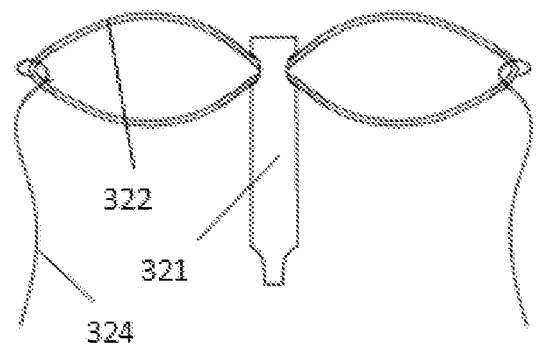

Referring to FIGS. 11E and 11F, as another embodiment, the second clamping member control device 224 is a sleeve. The second clamping member 222 is restricted in the second clamping member control device 224. When the sleeve 224 is pulled in the axial direction to move toward the proximal end relative to the second clamping member 222, the second clamping member 222 can be released.

Referring to FIGS. 12A to 12D, in order to achieve the above-described technical solutions, the present application also provides a delivery system 260 for the stepwise-clamping type valve prosthesis. The delivery system includes a stepwise-clamping type valve prosthesis 200, an outer sheath 261, a frame sheath 262, a frame sheath core 263, and a clamping member sheath 264. The stepwise-clamping type valve prosthesis 200 includes a frame body 210 and at least one clamping member 220. The frame body 210 has a channel allowing blood to flow therethrough. The clamping member 220 includes a first clamping member 221 and a second clamping member 222. One end of the first clamping member 221 is connected to the frame body 210, and the other end of the first clamping member 221 is a free end. The second clamping member 222 is connected to the first clamping member 221. The valve prosthesis 200 further includes a valve leaflet body 230. The valve leaflet body 230 allows blood to pass in one direction and blocks its regurgitation. The valve leaflet body 230 is pre-fixed inside the frame body 210. The frame sheath 262 and the clamping member sheath 264 are arranged in the outer sheath 261. The clamping member sheath 264 is arranged between the outer sheath 261 and the frame sheath 262. The frame body 210 is arranged at the distal end of the frame sheath 262 and partly located outside the frame sheath 262. The frame sheath core 263 is arranged in the frame sheath 262. The distal end of the clamping member sheath 264 and the distal end of the second clamping member control device 224 are both flexible. This design is to make the distal ends of the clamping member sheath 264 and the second clamping member control device 224 adaptable to the deformation of the clamping member 220. As an embodiment, the second clamping member control device 224 is a wire. One end of the wire is connected to the second clamping member control device operating member 270, and the other end of the wire 224 is detachably connected to an end of the second clamping member 222. The wire 224 is arranged in the clamping member sheath 264. The first clamping member 221 after being compressed is located at the distal end of the clamping member sheath 264. The proximal end of the outer sheath 261 is connected to an outer sheath operating member 2610. The proximal end of the frame sheath 262 is connected to a frame sheath operating member 2620. The proximal end of the frame sheath core 263 is connected to a frame sheath core operating member 2630. The proximal end of the clamping member sheath 264 is connected to a clamping member sheath operating member 2640.

The first clamping member 221 and the second clamping member 222 have three states from being restricted to being fully released. In the first state, the first clamping member 221 is restricted in the clamping member sheath 264, and the second clamping member 222 is restricted in the first clamping member 221. In the second state, by operating the clamping member sheath operating member 2640, the first clamping member 221 is extended in the radial direction of the frame body 210 to reach the position between the valve leaflet and the heart wall. In the third state, by operating the second clamping member control device operating member 270, the second clamping member 222 is protruded from the first clamping member 221 and circumferentially surrounds and abuts against the outer surface of the frame body 210, and the autologous valve leaflet and adjacent tissues are clamped between the second clamping member 222, the first clamping member 221, and the frame body 210.

The operation process of the valve prosthesis delivery system 260 in the present application is described step by step as follows.

(1) Referring to FIGS. 13A to 13B, Step 1: Withdrawing the Outer Sheath After the valve prosthesis is delivered to the target site of the patient, the outer sheath operating member 2610 is operated to make the outer sheath 261 slide in the axial direction toward the proximal end until the distal part of the frame body 210 is released and deployed. The deployed portion of the frame body 110 is adjusted such that it is positioned on the patient's valve annulus and abuts against the atrial tissue.

(2) Referring to FIGS. 14A to 14B, Step 2: Releasing the First Clamping Member The clamping member sheath operating member 2640 is operated to move the clamping member sheath 264 in the axial direction toward the proximal end until the first clamping member 221 is released. An opening angle is predetermined between the first clamping member 221 and the frame body 210. After the clamping member sheath 264 is removed, the first clamping member 221 is deviated to the predetermined angle from the frame body 210. At this time, the first clamping member 221 reaches the positions between the leaflet and the ventricular wall from the commissure between the anterior leaflet and the posterior leaflet.

(3) Referring to FIGS. 15A to 15B, Step 3: Releasing the Second Clamping Member The second clamping member control device operating member 270 is pulled to move the wire 224 toward the proximal end. The wire 224 further pulls the second clamping member 222 to protrude out from the outlet 2212. The second clamping member control device operating member 270 is continuously pulled until the detach-preventing end 2224 finally passes the stopper 2213, then the second clamping member 222 is completely released. The second clamping member 222 surrounds the frame body 210 with its two lateral wings in the predetermined shape. The valve leaflet and chordae tendineae are partially clamped between the second clamping member 222 and the outer surface of the frame body 210. After confirmation, the wire 224 and the second clamping member 222 are disconnected from each other through the releasable knot, and the wire 224 is pulled out.

(4) Referring to FIGS. 16A to 16B, Step 4: Releasing the Frame Body Completely

The frame sheath operating member 2620 is operated to make the frame sheath 262 slide in the axial direction toward the proximal end, so that the frame body 210 is completely released and deployed. The patient's valve leaflets and adjacent chordae tendineae are clamped between the first clamping members 221, the second clamping members 222, and the frame body 210.

(5) Referring to FIG. 17, Step 5: Withdrawing the Delivery System

The outer sheath operating member 2610 is operated to make the outer sheath 261 slide in the axial direction toward the distal end until the distal end of the outer sheath 261 touches a guiding tip, and then the delivery system 260 is withdrawn from the human body via the apex of the heart.

Example 3

Referring to FIGS. 18A to 18D, as another embodiment, a stepwise-clamping type valve prosthesis 300 is different from the above-described embodiments in that the valve leaflet body 330 is not pre-fixed onto the frame body 310, but is released inside the frame body 310 after the frame body 310 is completely released. In order to achieve the above technical solution, the present application also provides a delivery system 360 for the stepwise-clamping type valve prosthesis. The delivery system includes a stepwise-clamping type valve prosthesis 300, an outer sheath 361, a frame sheath 362, a frame sheath core 363, and a clamping member sheath 364. The stepwise-clamping type valve prosthesis 300 includes a frame body 310 and at least one clamping member 320. The frame body 310 has a channel allowing blood to flow therethrough. The clamping member 320 includes a first clamping member 321 and a second clamping member 322. One end of the first clamping member 321 is connected to the frame body 310, and the other end of the first clamping member 321 is a free end. The second clamping member 322 is connected to the first clamping member 321. The valve leaflet body 330 is loaded in the frame sheath 362 and located at the proximal end of the frame body 310. The positions of the leaflet body 330 and the frame body 310 in the frame sheath 362 do not overlap. The advantage of this design is that the sizes of the sheaths can be further decreased. The frame sheath 362 and the clamping member sheath 364 are arranged in the outer sheath 361. The clamping member sheath 364 is arranged between the outer sheath 361 and the frame sheath 362. The frame body 310 is arranged at the distal end of the frame sheath 362 and partly located outside the frame sheath 362. The frame sheath core 363 is arranged in the frame sheath 262. The second clamping member control device 324 is a wire. One end of the wire is detachably connected to the second clamping member control device operating member 370, and the other end of the wire 324 is connected to an end of the second clamping member 322. The wire 324 is arranged in the clamping member sheath 364. The first clamping member 321 after being compressed is located at the distal end of the clamping member sheath 364. The proximal end of the outer sheath 361 is connected to an outer sheath operating member 3610. The proximal end of the frame sheath 362 is connected to a frame sheath operating member 3620. The proximal end of the frame sheath core 363 is connected to a frame sheath core operating member 3630. The proximal end of the clamping member sheath 364 is connected to a clamping member sheath operating member 3640. The valve leaflet body 330 is released through a valve leaflet body operating member 3650.

The first clamping member 321 and the second clamping member 322 have three states from being restricted to being fully released. In the first state, the first clamping member 321 is restricted in the clamping member sheath 364, and the second clamping member 322 is restricted in the first clamping member 321. In the second state, by operating the clamping member sheath operating member 3640, the first clamping member 321 is extended in the radial direction of the frame body 310 to reach the position between the valve leaflet and the heart wall. In the third state, by operating the second clamping member control device operating member 370, the second clamping member 322 is protruded from the first clamping member 321 and circumferentially surrounds and abuts against the outer surface of the frame body 310, and the autologous valve leaflet and adjacent tissues are clamped between the second clamping member 322, the first clamping member 321, and the frame body 310.

The operation process of the valve prosthesis delivery system 360 in the present application is described step by step as follows.

Figure 19A:
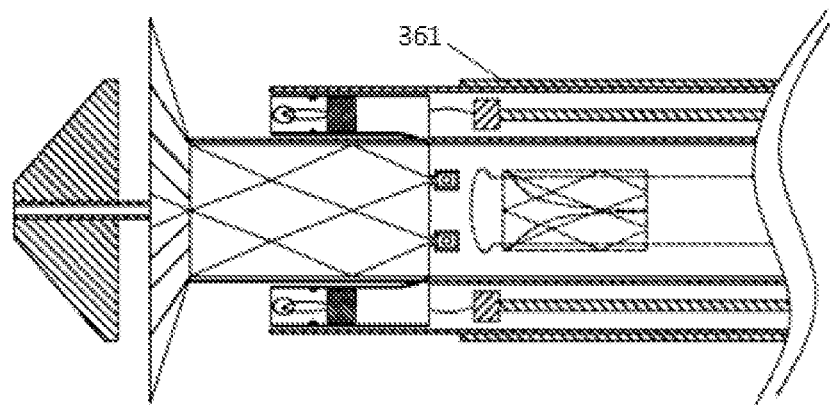
FIGS. 19A to 19G are schematic views of another embodiment of the delivery system of the present application.

(1) Referring to FIG. 19A, Step 1: Withdrawing the Outer Sheath

After the valve prosthesis is delivered to the target site of the patient, the outer sheath operating member 3610 is operated to make the outer sheath 361 slide in the axial direction toward the proximal end until the distal part of the frame body 310 is released and deployed. The deployed portion of the frame body 110 is adjusted such that it is positioned on the patient's valve annulus and abuts against the atrial tissue.

Figure 19B:
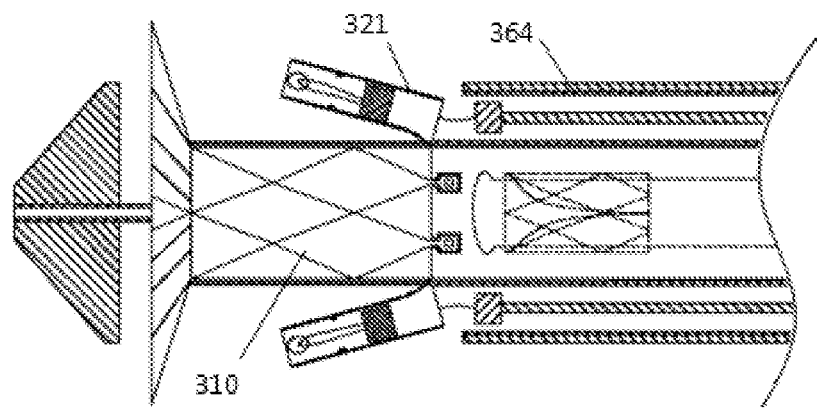

(2) Referring to FIG. 19B, Step 2: Releasing the First Clamping Member

The clamping member sheath operating member 3640 is operated to move the clamping member sheath 364 in the axial direction toward the proximal end until the first clamping member 321 is released. The first clamping member 321 is deviated to the predetermined angle from the frame body 310. At this time, the first clamping members 321 reach the positions between the leaflets and the ventricular wall from the region A1 of the anterior leaflet and the region P3 of the posterior leaflet (as shown in FIG. 1B).

Figure 19C:
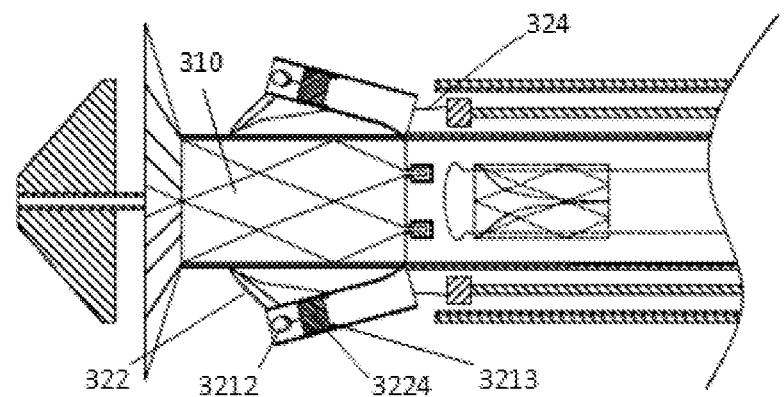

(3) Referring to FIG. 19C, Step 3: Releasing the Second Clamping Member

The second clamping member control device operating member 370 is pulled to move the wire 324 toward the proximal end. The wire 324 further pulls the second clamping member 322 to protrude out from the outlet 3212. The second clamping member control device operating member 370 is continuously pulled until the detach-preventing end 3224 finally passes the stopper 3213, then the second clamping member 322 is completely released. The second clamping member 322 surrounds the frame body 310 with its two lateral wings in the predetermined shape. The valve leaflet and chordae tendineae are partially clamped between the second clamping member 322 and the outer surface of the frame body 310.

Figure 19D:
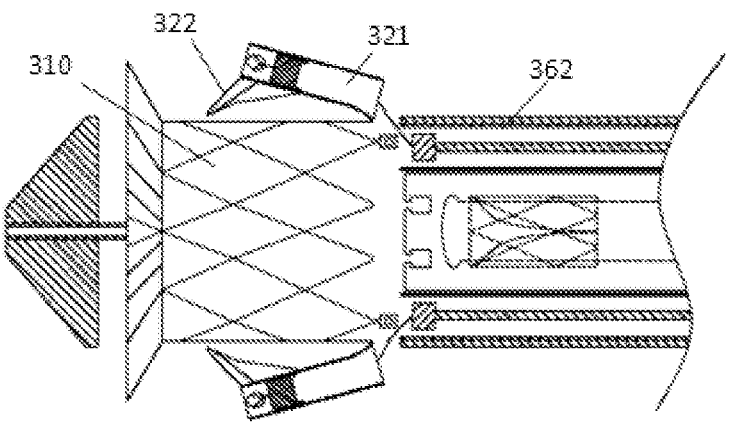

(4) Referring to FIG. 19D, Step 4: Releasing the Frame Body Completely

The frame sheath operating member 3620 is operated to make the frame sheath 362 slide in the axial direction toward the proximal end, so that the frame body 310 is completely released and deployed. The patient's valve leaflet and adjacent chordae tendineae are clamped between the first clamping member 321, the second clamping member 322, and the frame body 310.

Figure 19E:
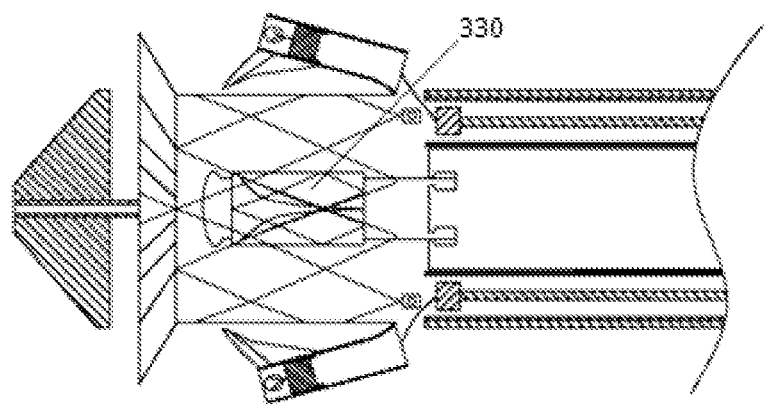
Figure 19F:
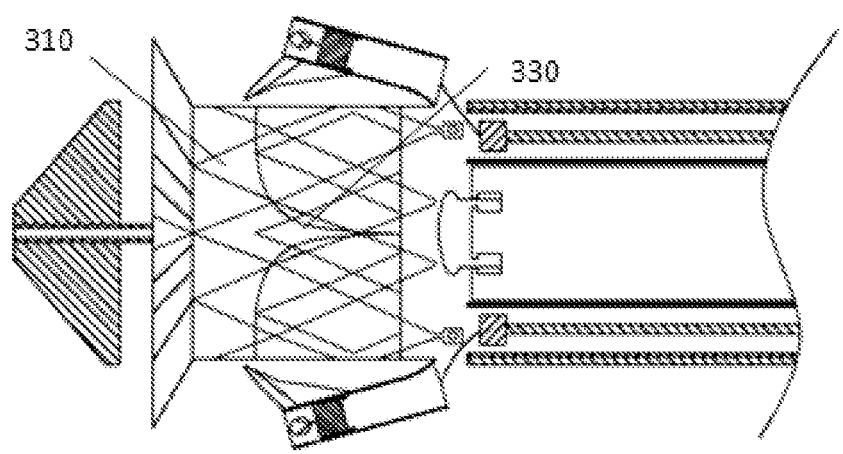

(5) Referring to FIG. 19E and FIG. 19F, Step 5: Releasing the Valve Leaflet Body By operating the valve leaflet body operating member 3650, the valve leaflet body 330 is pushed in the axial direction. The valve leaflet body 330 can be a commercially available cylindrical self-expanding valve or a balloon-expandable valve. Generally, the leaflet body 330 would be pre-fixed on a leaflet support. The valve leaflet body 330 is released into the frame body 310. When the position is correct, the wire 324 and the second clamping member control device operating member 370 are disconnected from each other.

Figure 19G:
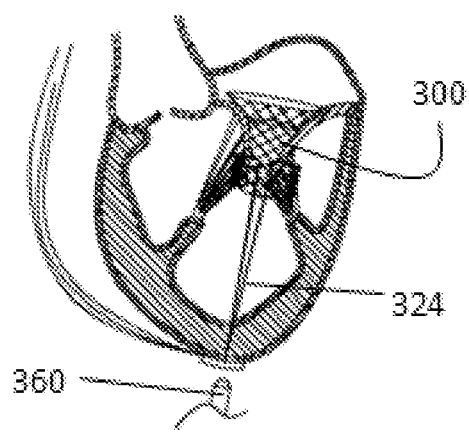

(6) Referring to FIG. 19G Step 6: Withdrawing the Delivery System

The outer sheath operating member 3610 is operated to make the outer sheath 361 slide in the axial direction toward the distal end until the distal end of the outer sheath 361 touches a guiding tip, and then the delivery system 360 is withdrawn from the human body via the apex of the heart. The wire 324 is withdrawn from the delivery system 360 and sutured at the apex of the heart.

In addition to the mitral valve, the technical schemes of the present application can also be applied to treat the patients with the diseases of the tricuspid valve, the aortic valve, and the pulmonary valve.

The technical features of the above-described embodiments can be combined arbitrarily. In order to make the description concise, not all possible combinations of the technical features in the above embodiments are described. However, these combinations of the technical features should be considered within the scope of the present application, as long as there is no contradiction among them.

What described above are only several embodiments of the present application. These embodiments are specific and detailed, but not intended to limit the scope of the present application. It should be understood by one ordinary skill in the art that various modifications and improvements can be made without departing from the conception of the present application, and all fall within the protection scope of the present application. Therefore, the patent protection scope of the present application is defined by the appended claims.

What is claimed is:

1. A stepwise-clamping type valve prosthesis, comprising:
a frame body; and
a clamping member,
wherein the frame body has a channel allowing blood to flow therethrough, the clamping member comprises:
a first clamping member; and
a second clamping member;
wherein one end of the first clamping member is connected to the frame body, and another end of the first clamping member is a free end; the second clamping member is connected to the first clamping member;
the clamping member has three states in sequence from being restricted to being fully released; in the first state, the first clamping member and the second clamping member are both restricted; in the second state, the second clamping member is restricted, and the first clamping member extends in a radial direction of the frame body and is capable of reaching a position between a valve leaflet and a heart wall; in the third state, the second clamping member protrudes from the first clamping member and extends in a circumferential direction of the frame body and abuts against an outer surface of the frame body, so that a natural valve leaflet and adjacent tissues are capable of being clamped between the second clamping member, the first clamping member, and the frame body;
wherein the stepwise-clamping type valve prosthesis comprises a second clamping member control device configured to release the second clamping member, and the second clamping member control device is detachably connected to the second clamping member.

2. The stepwise-clamping type valve prosthesis according to claim 1, wherein the first clamping member is a hollow structure, and the second clamping member in a restricted state is arranged in the first clamping member.

3. The stepwise-clamping type valve prosthesis according to claim 2, wherein the second clamping member control device is arranged in the first clamping member.

4. The stepwise-clamping type valve prosthesis according to claim 3, wherein the second clamping member control device is a push rod, the second clamping member has a detach-preventing end, and the push rod is detachably connected to the detach-preventing end.

5. The stepwise-clamping type valve prosthesis according to claim 4, wherein the second clamping member comprises two lateral wings, one end of each of the lateral wings is connected to the first clamping member, and the other end of the each of the lateral wings is connected to the detach-preventing end, the first clamping member is provided with outlets, and the lateral wings respectively protrude from the outlets.

6. The stepwise-clamping type valve prosthesis according to claim 5, wherein a side wall of the first clamping member is provided with a stopper, the stopper is a one-way protrusion.

7. The stepwise-clamping type valve prosthesis according to claim 1, wherein the second clamping member is arranged on an outer surface of the first clamping member.

8. The stepwise-clamping type valve prosthesis according to claim 7, wherein the second clamping member control device is arranged outside the first clamping member.

9. The stepwise-clamping type valve prosthesis according to claim 8, wherein the second clamping member control device is a wire.

10. The stepwise-clamping type valve prosthesis according to claim 9, wherein the second clamping member is bound to the surface of the first clamping member by the wire, the second clamping member is capable of being released by loosening a releasable knot, drawing the wire, or cutting the wire.

11. The stepwise-clamping type valve prosthesis according to claim 8, wherein the second clamping member control device is a sleeve.

12. The stepwise-clamping type valve prosthesis according to claim 1, further comprising a valve leaflet body arranged in the frame body.

13. The stepwise-clamping type valve prosthesis according to claim 12, wherein the valve leaflet body is pre-fixed in the frame body, or the valve leaflet body is released into the frame body after the frame body is completely released.

14. A delivery system of the stepwise-clamping type valve prosthesis according to claim 1, comprising:
the stepwise-clamping type valve prosthesis,
an outer sheath,
a frame sheath,
a frame sheath core, and
a clamping member sheath,
wherein the frame sheath and the clamping member sheath are arranged in the outer sheath, the clamping member sheath is arranged between the outer sheath and the frame sheath, the frame body is arranged at a distal end of the frame sheath and partly located outside the frame sheath, the frame sheath core is arranged in the frame sheath, the second clamping member control device is arranged in the clamping member sheath, the first clamping member that is compressed is located at a distal end of the clamping member sheath, a proximal end of the outer sheath is connected to an outer sheath operating member, a proximal end of the frame sheath is connected to a frame sheath operating member, a proximal end of the frame sheath core is connected to a frame sheath core operating member, a proximal end of the clamping member sheath is connected to a clamping member sheath operating member, and one end of the second clamping member control device is connected to a second clamping member control device operating member, the first clamping member and the second clamping member have three states in sequence from being restricted to being fully released; in the first state, the first clamping member and the second clamping member are both restricted; in the second state, by operating the clamping member sheath operating member, the first clamping member is extended in the radial direction of the frame body and is capable of reaching the position between the valve leaflet and the heart wall; in the third state, by operating the second clamping member control device operating member, the second clamping member is protruded from the first clamping member and circumferentially surrounds and abuts against the outer surface of the frame body, so that the natural valve leaflet and the adjacent tissues are capable of being clamped between the second clamping member, the first clamping member and the frame body.

15. The delivery system according to claim 14, wherein in the first state, the first clamping member is restricted in the clamping member sheath, and the second clamping member is restricted in or outside the first clamping member.

* * * * *